United States Patent [19]

Lew

[11] Patent Number: 4,568,639

[45] Date of Patent: Feb. 4, 1986

[54] METHOD FOR THE COMMERCIAL PRODUCTION OF HELMINTHS ANTIGENS

[76] Inventor: Kenneth K. Lew, 90 Park St., Brookline, Mass. 02146

[21] Appl. No.: 703,759

[22] Filed: Feb. 21, 1985

Related U.S. Application Data

[63] Continuation of Ser. No. 399,718, Jul. 19, 1982, abandoned.

[51] Int. Cl.$^4$ .................. C12P 21/00; C12N 15/00; A01K 45/00; A61K 39/00
[52] U.S. Cl. .................... 435/68; 435/172.1; 119/1; 424/88; 424/95; 436/543
[58] Field of Search .............. 435/172.1, 68; 119/1; 424/88, 95; 436/543

[56] References Cited

U.S. PATENT DOCUMENTS 4,396,600 8/1983 Messiner et al. ............... 424/85

OTHER PUBLICATIONS

Desowitz et al, Journal of Helminthology, vol. 50, pp. 53–57 (1976).
Hirsh et al, Developmental Biology, vol. 49, pp. 220–235 (1976).
Lew et al, Environ Mutagen, p. 265 (1980).
Lew et al, Environ Mutagen, p. 346 (1981).
Edgar et al, Science, vol. 198, pp. 1285 & 1286 (1977).
Emmons et al, PNAS, vol. 76, pp. 1333–1337, Mar. 1979.
Filijev, Smithsonian Miscellaneous Collections, vol. 89, No. 6, Mar. 20, 1934.

*Primary Examiner*—Alvin E. Tanenholtz
*Attorney, Agent, or Firm*—Thompson, Birch, Gauthier & Samuels

[57] ABSTRACT

An easily cultured worm is genetically modified such that its surface antigens on its modified form are immunologically identical to the surface antigens of a parasitic worm. Specifically, *C. elegans* is genetically modified to produce antigens corresponding to the antigens of *D. immitis* which causes heartworm infection. The antigens derived from the easily cultured worm are used to form a vaccine and/or diagnostic.

9 Claims, No Drawings

METHOD FOR THE COMMERCIAL PRODUCTION OF HELMINTHS ANTIGENS

This is a continuation of co-pending application Ser. No. 399,718 filed on July 19, 1982, now abandoned.

BACKGROUND OF THE INVENTION

This invention relates to the development and commercial production of helminths (parasitic worm) antigens.

The use of antigens for diagnostics and vaccines to detect and prevent infectious diseases such as polio, smallpox, diphtheria, tetanus and hoof and mouth diseases has been clearly shown in both humans and animals. Most antigens used as diagnostics and vaccines are derived from cultured infectious organisms. The infectious organisms are grown in vitro or in vivo in animals or tissue cultures. An example is polio antigens which are derived from viruses grown in vitro in monkey kidney cells. The antigens are used as a diagnostic and to vaccinate humans.

If a small amount of attenuated viruses is inoculated in a host, the inoculated viruses which carry specific antigens will induce antibody formation in the host which in the future will recognize and destroy future invading polio viruses. The same polio virus antigens can also be used for the diagnosis of a polio infection. If a host is infected by polio, some specific antibodies will be elicited in the body and the presence of these antibodies will be indicative of an infection. The detection of antibodies can be assayed for their binding to polio antigens with the standard immunofluoroscent, radioimmune, and enzyme-linked, immunoelectrophoresis, hemagglutinin and immunodiffusion assays.

It is not possible, however, to commercially produce antigens for all infectious diseases. One limitation of production has been the inability to cultivate or produce a large amount of infectious organisms in vivo or in vitro from which the antigens are derived This is especially true for vaccines in which the infectious organisms have complicated life cycles and/or have more than one host. Most parasitic worm diseases that infect dogs, cats, sheep, pigs, horses and humans fall into this category An example is the helminths disease of the heartworm which can infect a wide variety of organisms from dogs, cats, seals to humans (infrequently). The parasite, however, generally resides in the dog as its host with the mosquito as its intermediate host. It would be difficult to derive antigens necessary in the manufacture of vaccines or diagnostics since the parasitic worm undergoes several stages of larval development and only one larval stage contains the appropriate antigens. In the heartworm this particular stage, the infectious larvae, resides in the mosquito. Under these conditions, the capture of the intermediate hosts (mosquitos) and the dissection for the infectious larvae is necessary to generate required antigens for the manufacture of a heartworm vaccine. Wong, M. M., Guest, M. F., and Laviopierre, M. J. (1974) *Dirofilaria immitis;* Fate and Immunogenicity of Irradiated Infective Stage Larvae in Beagles *Experimental Parasitology* 35, 65–74. Similarly, antigens which are necessary to diagnose heartworm antibodies for infection must be derived from adult heartworms harbored in the heart of an infected dog. Desowitz, R. S. and Una, S. R. (1976), The Detection of Antibodies in Human and Animal Filariasis by Counter-immunoelectrophoresis with *Dirofiliaria immitis* Antigen. *Journal of Helminthology,* 50, 53–57, Grieve, R. B., Mika-Johnson, M., Jacobson, R. H., and Raymond, C. H., (1981) Enzyme-Linked Immunosorbent Assay for Measurement of Antibody Response to *Dirofilaria immitis* in Experimentally Infected Dogs. *American Journal of Veterinary Research,* 42, 66–69. These sources and methods of generating heartworm antigens for diagnostics (from the heart of a dog) and vaccines (from mosquitos) are neither commercially feasible nor may they be socially acceptable.

I have devised a method of producing helminths (parasitic worm) antigens wherein a related species of the infectious worm that can be easily cultured is genetically modified. The method involves identifying the surface antigens of the difficult to culture parasitic worm and then creating these same antigens in the easily cultured species.

The easily cultured species is genetically altered through mutations until said species have some of the same immunological antigens of the difficult to culture parasitic worm. Through these genetic manipulations, the types and amounts of antigens of interest in the easily cultured species are altered. Antigens derived from the genetically altered species are then used for the commercial production of antigens necessary for the manufacture of diagnostics and vaccines.

The principle of my invention is to alter the antigen genes of the easily cultured species to produce preferably in situ antigens of the hard to culture parasitic species. The expression of these altered genes to produce these antigens can also occur in bacteria or yeast with the cloning of the antigen genes, and thus, provide a potentially more efficient production of these same antigens.

In the preferred embodiments, the antigens produced using this invention against the heartworm infection is by *Dirofilaria immitis,* and the substituted related species is the free-living hermaphroditic nematode *Caenorhabditis elegans.*

DESCRIPTION OF THE PREFERRED EMBODIMENT

Generation of antibodies against heartworm antigens of *Dirofilaria immitis*

Antibodies must be first generated against parasitic antigens of interest. These antibodies which recognize and bind specifically to the hard to culture parasitic antigens can then be used as a probe to isolate mutants in the easily cultured species which are capable of producing the corresponding parasitic antigens. In the examples set forth below, I have generated antibodies against adult heartworm antigens and isolated mutants in *C. elegans* with the corresponding heartworm antigens. Although described in reference to *C. elegans,* other species which are believed suitable are *Panagrellas redivious, Turbatric acetic* and *C. briggsae.*

Adult heartworms were isolated from a dog infected with heartworm. The adult heartworms were excised from the heart and suspended in 0.15 M phosphate buffered saline pH 7.4 (PBS). The heartworms were homogenized and the homogenate was adjusted to a final concentration of 500 micrograms of protein (wet weight) per ml of PBS. This homogenate was then mixed with equal volume of Freund's complete adjuvant. A 2 ml sample of this mix was used to immunize a rabbit for heartworm antigens. Before actual immunization, a preimmune serum was drawn from the rabbit.

The rabbit was inoculated at days 25 and 35 after the first immunization with 2 ml of a mixture of equal volume of homogenate and Freund's incomplete adjuvant. After a positive test bleed at 45 days, the serum was collected and used to assay for antibody formation against heartworm antigens used for the immunization.

Assay of serum containing anti-heartworm antibodies.

The serum of the rabbit immunized with heartworm antigens was assayed for antibody activities against heartworm antigens and C. elegans antigens. My preferred method is to use a immunofluorescent assay of conjugated fluoroscein or rhodamine goat anti-rabbit IgG. Other methods such as enzyme-linked, radioimmune, hemagglutinin and immundiffusion assay can also be used. Sections of heartworm tissues from dogs (containing the antigens) were washed three times with PBS and then incubated with the rabbit anti-heartworm antibodies at room temperature for 30 minutes, the tissues were then washed 3 times with PBS to remove the rabbit anti-heartworm antibodies. Following this, the tissues were incubated with fluoroscein goat anti-rabbit IgG antibodies. After incubation, the free goat anti-rabbit IgG antibodies were removed by washing the heartworm tissues 3 times with PBS. The presence of rabbit antibody activities binding to specific heartworm antigens was indicated by the binding of the fluoroscent goat anti-rabbit IgG antibodies which were then observed in a fluoroscent microscope, red (rhodamine) or green (fluorescein) in color.

C. elegans whole animals and tissues were also used to assay the anti-heartworm antibodies generated by the immunized rabbit serum. The results of the fluoroscent assays for anti-heartworm activities are summarized in Table I.

The control preimmune serum had no activity against either heartworm tisues or C. elegans tissues. In contrast, there was evidence of antibody activities in the immunized rabbit serum against heartworm tissues but not C. elegans. Thus, the generation of antibodies against heartworm antigens is only specific for heartworm but not C. elegans. This serum which appears specific was used as a probe to isolate mutants of C. elegans which will, in accordance with my invention, carry antigens corresponding to heartworm antigens.

TABLE I

Antibody activities of serum from a rabbit which has been immunized with heartworm antigens

|  | Immune Serum | | Preimmune Serum | |
| --- | --- | --- | --- | --- |
| Titer | Heartworm tissue | C. elegans tissue | Heartworm tissue | C. elegans tissue |
| 1:5 | + | − | − | − |
| 1:20 | + | − | − | − |
| 1:40 | + | − | − | − |
| 1:80 | + | − | − | − |
| 1:160 | + | − | − | − |

+ = fluorescent activity
− = no activity

TABLE II

Antibody binding activity of six independently isolated mutants of C. elegans with 1:50 titer of rabbit anti-heartworm serum

|  | Immune Serum | Preimmune Serum |
| --- | --- | --- |
| Wild Type (C. elegans) | − | − |
| Heartworm Mutant Strain | + | − |

TABLE II-continued

Antibody binding activity of six independently isolated mutants of C. elegans with 1:50 titer of rabbit anti-heartworm serum

|  | Immune Serum | Preimmune Serum |
| --- | --- | --- |
| VGI-1 | + | − |
| VGI-2 | + | − |
| VGI-3 | + | − |
| VGI-4 | + | − |
| VGI-5 | + | − |
| VGI-6 | + | − |

TABLE III

Antibody binding activity of one mutant VGI-6 with rabbit anti-heartworm serum

| Titer | VGI-6 tissue | Heartworm tissue | Wild Type (C. elegans) tissue |
| --- | --- | --- | --- |
| 1:5 | + | + | − |
| 1:20 | + | + | − |
| 1:40 | + | + | − |
| 1:80 | + | + | − |
| 1:160 | + | + | − |

Mutagenization of C. elegans to generate mutants which have altered antigens that correspond to heartworm antigens The free-living soil nematode C. elegans is preferred since it can be readily cultured in large quantities and homozygous recessive mutations can be generated. Brenner, S. (1974), The Genetics of Caenorhabditis elegans Genetics 77, 71–94. This is due to the hermaphroditic nature of the animal, that is, it is self-fertilizing. A mutation introduced in the animal upon self-fertilization for two generations will produce a homozygous mutation.

Young larvae of C. elegans at the first and second larval stage of development were exposed to the mutagen, ethyl methyl sulfonate (any other mutagens can also be used, such as methyl methane sulfonate, acridine orange, nitrosoguanidine, hydroxynitrosamine; Drake, J. W. and R. H. Baltz (1976), The Biochemistry of Mutagenesis, Annual Review of Biochemistry 45, 11) and allowed to self-fertilize and lay eggs. The $F_1$ generation of this mutagenesis was allowed to reproduce and the $F_2$ generation was then screened for animals which would bind to antibodies made against specific antigens of the heartworm. Because wild type C. elegans do not bind to antibodies made against heartworm antigens generated in our rabbit heartworm antiserum (See Table I), a visual screen was made for mutants that had antigens that bound to the heartworm antibodies using the above fluorescent assay. Mutants which bound to the heartworm antibodies unlike the wild type (with no fluorescence) had a fluorescent color of red (rhodamine) or green (fluorescein). These mutant animals were removed and cloned.

Animals which breed true for this characteristic are considered to be mutants which have an altered gene that would produce an antigen(s) corresponding to those of the heartworm.

Using the above methods, I have demonstrated with my invention, in Table II, that mutants of *C. elegans* with altered antigens corresponding to those of heartworm antigens can be generated. The antibody binding activities with anti-heartworm serum of six (6) independently isolated mutants is compared with heartworm tissues and wild type tissues in Table II.

Table III represents a further characterization of one of the representative mutants among the six (6) in Table II in which the binding of antibody activity behave very closely to heartworm tissue.

Furthermore, when one of these C. elegans mutants was immunized to a rabbit, it was able to elicit an immunogenic response in which the antibodies produced in the serum had binding activities to a species of heartworm antigens.

Thus, the mutants isolated with my invention not only have an antigenic response of binding to heartworm antibodies, but also a immunogenic response in producing antibodies against heartworm antigens.

Using the above described method, I also isolated a mutant of *C. elegans* which was altered in at least some of its surface antigens to be immunologically identical to the antigens of another parasitic worm, *Ancylostoma caninum*, a hookworm which infests in the intestine of the dog.

Any worm species which are readily cultured and in which mutations can be introduced to cause an alteration in its antigens to a corresponding difficult to culture parasitic worm antigen can be used with my method.

Conceptually, using *C. elegans* and the heartworm, *D. immitis* as an example, once the antigens of the desired parasite are generated with the above method, they can be used to develop a range of diagnostics for the presence of antibodies induced upon a parasitic worm infection. Such an approach with heartworm antigens has been shown to be useful in the diagnosis of several types of helminths infections. *Desowitz and Una, supra;* Hedge and Ridley (1977). Immunofluorescent Reactions with Microfilariae. 1 Diagnostic Evaluation; Transaction of the Royal Society of Tropical Medicine and Hygiene 71, 304–307. In the case of the heartworm antigens which I have generated, I have found that one of the mutants isolated in *C. elegans,* VGI-2, is useful in the diagnosis of heartworm infection. When serum samples of dogs diagnosed as infected and uninfected with heartworms were assayed with the VGI-2 mutant, the results were remarkedly accurate in that 6 dogs diagnosed with the standard filter assay as positively infected based on the presence of microfilarie were also found to be positive in this mutant with the immunofluorescent assay. In contrast, 5 samples of serum from clinically diagnosed uninfected dogs were also found negative in the mutant. Besides the use of immunofluoroscent assay to detect parasitic worm infection with mutant antigens, enzyme-linked, radioimmune, immunodiffision or hemagglutinin assay can also be applied. D. Stites (1976), Laboratory Methods for Detection of Antigens and Antibodies, *Basic and Clinical Immunology,* Lange Medical Publications, pp. 281–315.

Antigens generated with the described method can also be used for the manufacture of parasitic worm vaccines. In the example of heartworm infection, it is known that the antigens derived from infectious larvae can be used as a vaccine for dogs against heartworm infection; Wong, M. M., Guest, M. F., and Lavoipierre, M. J. (1974) *Dirofilaria immitis;* Fate and Immunogenicity of Irradiated Infective Stage Larvae in Beagles *Experimental Parasitology* 35, 65–79. As long as antibodies can be specifically generated against these particular infectious larval antigens and mutants of *C. elegans* with corresponding antigens are isolated, these mutants can be used to derive the immunogenic antigens necessary for the production and manufacture of heartworm vaccine. The vaccine generated can then be suspended for example in a buffered saline and then used for injection subcutaneously or intramuscularly in an animal for providing immunity against heartworm infection. W. J. Herbert (1978), Laboratory Animal Techniques for Immunology in "Handbook of Experimental Immunology", Vol. 1 Immuno Chemistry, 3rd Edition, Editor, D. M. Weir, Blackwell Scientific Publishers, Oxford, London.

The basic principle of my method is to alter the gene(s) of a closely related worm species that is easy to culture to generate antigens of a difficult to culture parasitic worm. In the described embodiment, the concept of the generation of antigens are in situ in the species of the easily cultured worm. This concept can be extended further in the expression of antigens in another organism such as bacteria, yeast or other microorganisms which may provide a more efficient and productive yield of the desired antigens. The isolation of the antigen gene(s) and their insertion into bacteria with genetic vectors can be applied. The genes for example in *C. elegans* can be isolated by initially isolating the nucleic acid of the animal with the proteinase K-SDS method described by Emmons, S., Klass, M. R., and Hirsh, D. (1979); Analysis of the Constancy of DNA Sequences During Development and Evolution of the Nematode *Caenorhabditis elegans Proceeding of the National Academy of Sciences* 76, 1333–1337.

The poly A (RNA) is separated by ethanol precipitation and by binding to oligo(dT) cellulose according to Aviv and Leder (1972), Purification of Biologically Active Globin Messenger RNA by Chroatography on Oligothymidylic Acid Cellulose, *Proceedings of the National Academy of Science* 69, 1408–1412. The material binding to oligo(dT) celulose are that used to purify poly A (RNA) which codes for the antigen gene product. Since the poly A (RNA) will only hybridize to the DNA which codes for the antigen gene, this poly A (RNA) can be used to select recombinant poly A (DNA) molecules of *C. elegans* coding for the antigen gene of interest. These recombinant DNA molecules can then be inserted into bacteria or yeast with various genetic vector such as plasmids or bacteriophage to express the antigen gene and product of interest using the basic techniques described by Davis, R. W., Botstein, D., and Roth, J. R. (1980). A manual for genetic engineering—*Advanced Bacterial Genetics,* Cold Spring Harbor Laboratory, Cold Spring Harbor, New York).

There is a possibility that antigens produced by the natural parasites may be more potent or specific than those originating from *C. elegans* through genetic mutations. Thus, the cloning of the naturally hard to culture parasitic genes for their antigens in an microorganism may be advantageous. If the cloning approach described above is used, it would be extremely difficult if not impossible to accomplish. This is due to the limitation of the amount of parasitic tissues available to isolate the poly A (RNA) of interest. The poly A (RNA) is only present in tissues which are expressing the antigen. In the case of poly A (RNA) corresponding to the antigens of the infectious larvae of the heartworm, the tissues must be derived from larval animals dissected from captured mosquitos which harbor the parasites. The availability of infectious larval tissues necessary to isolate enough poly A (RNA) corresponding to their antigens is limited therefore, making the task of poly A (RNA) isolation extremely difficult, if not impossible. However, if we use the poly A (RNA) isolated from *C.*

*elegans* mutant that correspond to these antigens of interest, we can through hybridization of the heartworm DNA isolate the recombinant DNA genes corresonding to the heartworm infectious larvae antigens. The availability of heartworm DNA is not limited since all tissues have DNA containing all genes and a large quantity of tissue can be acquired from adult heartworms.

Having described my invention, what I now claim is:

1. A method for the production of parasitic helminth antigens which comprises:
   identifying the antigens of *D. immitis;*
   modifying genetically *C. elegans* until mutants are formed which mutants are characterized by antigens possessing immunological identity to the antigens of *D. immitis;*
   isolating at least one of the mutants so modified and cultivating at least one of said mutants.

2. The method of claim 1 which includes: isolating the antigens of said mutants.

3. The method of claim 1 which includes: identifying the mutants which have the immunological identity with the antigens of the *D. immitis* by:
   isolating those mutants which bind to antibodies generated by a host immunized with *D. immitis* antigens.

4. A method for the production of parasitic helminth antigens which comprises:
   identifying the antigens of *A. canium;*
   modifying genetically *C. elegans* until mutants are formed which mutants are characterized by antigens possessing immunological identity to the antigens of *A. canium;*
   isolating at least one of the mutants so modified and cultivating at least one of said mutants.

5. The method of claim 4 which includes:
   isolating the antigens of said mutants.

6. The method of claim 4 which includes:
   identifying the mutants which have the immunological identity with the antigens of the *A. canium* by:
   isolating those mutants which bind to antibodies generated by a host immunized with *A. canium* antigens.

7. A method for the production of parasitic helminth antigens which comprises:
   identifying the antigens of *D. immitis;*
   modifying genetically *C. briggsae* until mutants are formed which mutants are characterized by antigens possessing immunological identity to the antigens of *D. immitis;*
   isolating at least one of the mutants so modified and cultivating at least one of said mutants.

8. The method of claim 7 which includes:
   isolating the antigens of said mutants.

9. The method of claim 7 which includes:
   identifying the mutants which have the immunological identity with the antigens of the *D. immitis* by:
   isolating those mutants which bind to antibodies generated by a host immunized with *D. immitis* antigens.

* * * * *